United States Patent [19]

Vandervelden

[11] Patent Number: 4,856,530
[45] Date of Patent: Aug. 15, 1989

[54] CATHETER IDENTIFIER AND METHOD

[75] Inventor: Cornelius K. Vandervelden, Salt Lake City, Utah

[73] Assignee: Becton, Dickinson and Company, Franklin Lakes, N.J.

[21] Appl. No.: 50,668

[22] Filed: May 14, 1987

[51] Int. Cl.$^4$ ............................................. A61B 5/02
[52] U.S. Cl. ........................................ 128/692; 128/897
[58] Field of Search ............... 128/632, 691, 692, 748, 128/303.1; 279/1 TS

[56] References Cited

U.S. PATENT DOCUMENTS

| | | | |
|---|---|---|---|
| 4,407,298 | 10/1983 | Lentz et al. | 128/692 |
| 4,418,392 | 11/1983 | Hata | 128/748 |
| 4,446,715 | 5/1984 | Bailey | 128/748 |
| 4,502,488 | 3/1985 | Degironimo et al. | 128/692 |
| 4,580,557 | 4/1986 | Hertzmann | 128/303.1 |
| 4,611,601 | 4/1986 | Bowman | 128/748 |
| 4,691,703 | 9/1987 | Auth et al. | 128/303.1 |
| 4,720,907 | 1/1988 | Rapp | 274/1 TS |

FOREIGN PATENT DOCUMENTS 1200852  2/1986  Canada ............................. 128/748

Primary Examiner—Lee S. Cohen
Assistant Examiner—David Shay
Attorney, Agent, or Firm—Aaron Passman

[57] ABSTRACT

Disclosed is an automatic means for entering into a cardiac output computer a computation constant for a given size catheter. The technique involves the placement of a capacitor across the output terminals of a thermodilution catheter assembly. This capacitor does not effect temperature measurements. By means of software controlled switching in the cardiac output computer circuitry, the capacitance of this capacitor can be determined and can be used to indicate the catheter size. Disclosed also is the process used to set up and identify the catheter gauge.

12 Claims, 1 Drawing Sheet

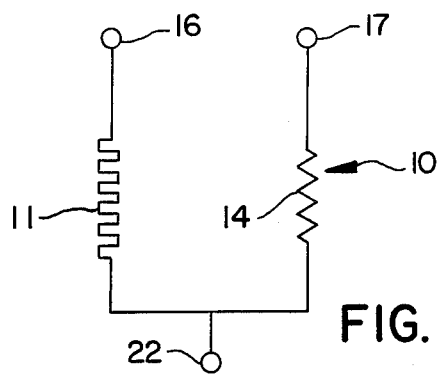
FIG. 1
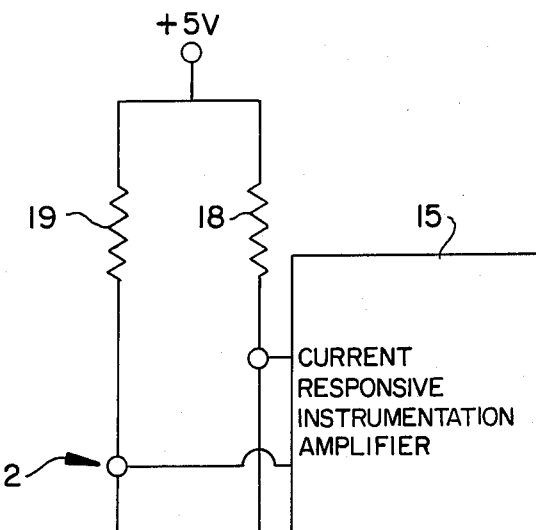
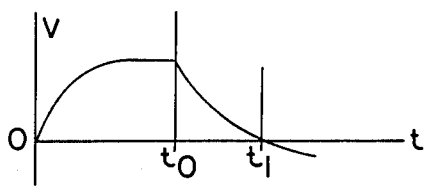
FIG. 4
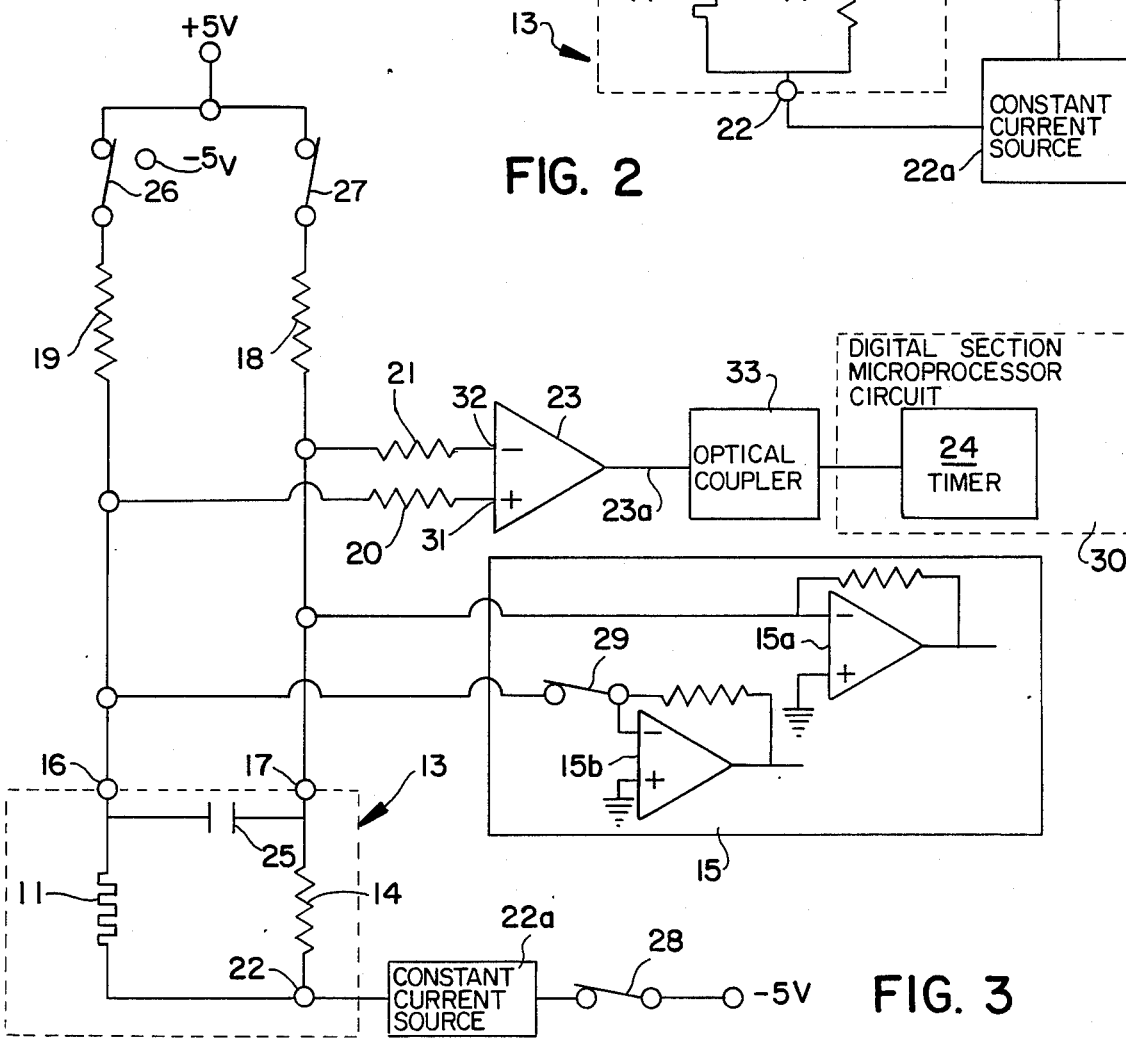
FIG. 2
FIG. 3

CATHETER IDENTIFIER AND METHOD

BACKGROUND OF THE INVENTION

This invention relates to thermodilution based methods for determining cardiac output. More specifically, to the technique used for identifying the particular type of the thermodilution catheter assembly connected to a cardiac output computer.

Thermodilution catheters have been used to determine cardiac output and these catheters are typically small diameter balloon types equipped with distal temperature sensing means and a lumen opening a short distance proximal to the temperature sensor for introduction of a low-temperature liquid injectate into the blood stream. The change in temperature resulting from the introduction of the low temperature injectate is sensed by the temperature sensing means, usually a thermistor. The magnitude and duration of the temperature change over time can be used to compute the blood flow rate for a measure of a patient's cardiac output. U.S. Pat. No. 3,995,623 shows a typical thermodilution catheter.

The blood flow rate is computed from the change in blood temperature according to the Stewart-Hamilton dilution equation for a thermal indicator as described in U.S. Pat. No. 3,987,788. As per that prior patent, numerical values are used for a computation constant, blood temperature, and injectate temperature. The computation constant is derived from the nature of the injectate, the volume of the injectate and a correction factor for the rise in temperature of the injectate as it passes through the lumen of the catheter to the injectate orifice. It is the size of the lumen in the catheter which must be known in order for the correct computation constant to be applied. With modern microprocessor technology, the computation constant for any given set of operating conditions can be programmed into the cardiac output computer by the manufacturer and it, therefore, becomes possible to automatically enter any variables affected by the catheter once the catheter has been identified.

In most cases, thermodilution blood flow measuring techniques are applied with a standard 5 percent glucose solution and one of a few of the standard injectate volumes for a given size catheter. The instructions for use of the computer can then specify that the injectate type and volume be entered. These required entries are known to the operator. The computation constant, on the other hand, must be looked up in the data that accompany the catheter and manually entered in the computer. Both the look-up and entering operations are prone to error.

In the prior art, there is U.S. Pat. No. 4,407,298 which discloses a thermodilution catheter identifier system having a specifically designed connector with a plurality of electrically conductive pins. The pins having connective bridge members to couple them selectively and thereby indicate the catheter size. In that system, three extra terminals are needed to accomplish a binary coded number of 1 to 4 in order to provide the requisite signal which indicates the size of catheter used. That system requires a terminal with five connector pins and although more complex has only four codes available.

It is accordingly an object of the present invention to provide an automatic means for entering the computation constant for a given size catheter injectate and injectate volume and temperature into the cardiac output computer when the catheter is connected. A manual override is provided in the event that a catheter of a non-standard size or a catheter which is not designed to automatically indicate its type by identifying itself is used with the cardiac output computer of the present invention.

SUMMARY OF THE DISCLOSURE

In order to solve the problems of the prior devices in a simplified manner, and to provide a technique for identifying catheters without the need for extra connector terminals, there is shown and disclosed herein a device which automatically configures the cardiac output computer in accordance with the catheter size used.

The present disclosure seeks to teach a system wherein no additional pins are required in the connector because of circuitry provided at the distal end of the catheter and responsive circuitry in the cardiac output computer. Notwithstanding these changes, the thermistor in the thermodilution catheter still functions with the cardiac output computer without interference from the identification and automatic setting circuitry.

In the present thermodilution type catheter assembly, the temperature sensing element, being a thermistor, is matched to a resistor network during the manufacture of the catheter assembly. The network, which may consist of a single resistor, is connected to the temperature sensing thermistor in order to maintain a constant resistance ratio notwithstanding manufacturing variations which cause operational tolerances in the thermistor. That is to say that, the resistance value of thermistor at a given temperature say, for example, 37° C. and that of the network resistance must be carefully matched because thermistor resistance values at that temperature may vary by as much as plus or minus 15 percent. An accurately maintained ratio between the network resistor and thermistor resistance at a given temperature assures linearity of the temperature measurement in spite of the fact that the thermistors used for temperature measurement usually exhibit a non-linear relationship between their resistance value and the measured temperature.

In operation the thermistor and the resistor are each connected to the input terminals of two operational amplifiers which are part of the analogue front end of the cardiac output computer. These input terminals are maintained at equal voltages by each operational amplifier as same respond to current changes at their inputs. Specifically the input terminals are maintained at the half-way voltage level of the analogue front end which is zero volts. This level could be referred to as "analogue ground", but in reality is insulated from actual or earth ground. The dynamic resistance between the terminals that power the thermistor and resistor and analogue ground is very low, only on the order of a few ohms. Connected to the junction of the thermistor and resistor is a constant current source which supplies a fixed current to the thermistor and the network resistor. Across the input terminals which are at the half-way voltage is a capacitor of a predetermined value for each catheter type. The capacitor will not affect the normal temperature measuring operation of the thermistor resistor network circuit in the catheter assembly because the voltage difference between the terminals is very small and stays so over the entire operating temperature range. Typically the voltage difference at the input terminals will be about 0.001 volt and varies less than that.

A typical cardiac output computer is equipped to measure the temperatures of blood and of a mixture of blood and injectate from thermistor data received from the end of the catheter. The computer described in this invention has in addition to the blood temperature measuring circuitry the capability of performing catheter identification. When the cardiac output computer is arranged, under software control, to measure the blood temperature, the instrumentation amplifiers are configured as already described. When it is required to measure the capacitance of the identification capacitor incorporated in the catheter assembly circuit, then the terminals of the instrumentation amplifiers are configured differently, again under software control.

The process of identification is in two phases; the first set up, the second identification. During the set-up phase, a series of switches, which are normally closed, are changed simultaneously to the open condition. This disconnects the catheter from the constant current source; prevents the low dynamic input impedance at the resistor terminal from exceeding its dynamic range while at the same time allowing the input impedance at the thermistor terminal to reach a high value. Consequently, the thermistor terminal will attain a voltage slightly higher than that of the resistor terminal. This is so because a resistor in the bridge circuit charges the capacitor through the voltage divider formed thereby in conjunction with the thermistor and the matching resistor. The resistor terminal is kept essentially at analogue ground.

A comparator detects this charging condition by virtue of the fact that it responds to very small differences in voltage between its inverting and noninverting inputs. Because the terminal for the thermistor is at a higher potential than the terminal for the resistor, the output of the comparator will be high. The set up duration is long enough to assure that the capacitor is fully charged.

The identification phase begins after the microprocessor has allowed sufficient charge duration. A switch opens which changes the circuit to charge the capacitor in an opposite direction. At the same instant that switch opens, a timer is started. The thermistor terminal voltage drops at a rate determined by the value of the capacitor and the sum of the values of the thermistor and the network resistor. The comparator detects the condition where the voltage across the capacitor is essentially zero. At this point in time, the output of the comparator goes from high to low and stops the timer. The amount of time measured by the timer is an indication of the particular type of catheter used as it is a measure of the unique value of the capacitor selected for that type of catheter.

Because this system is temperature dependent as it includes the thermistor, a range of capacitor discharge times are assigned for each type of catheter and the selection of particular capacitors is made in accordance with the understanding of this effect. Various capacitor values are selected which will space the particular types of catheters far enough apart in the timing sequence to make each easily recognizable.

BRIEF DESCRIPTION OF THE DRAWINGS

FIG. 1 is a typical thermodilution catheter temperature sensing circuit showing the thermistor and the resistor in parallel with one another and connected across common input terminals.

FIG. 2 shows the thermodilution catheter sensing circuit of FIG. 1 as connected to an instrument such as a cardiac output computer for use in measurement of temperature.

FIG. 3 shows the circuitry shown in FIG. 2 with the addition of the specific circuits necessary for catheter assembly identification.

FIG. 4 is a graph showing capacitor charge/decay versus time.

DETAILED DESCRIPTION OF THE DRAWINGS

In FIG. 1, the temperature sensing circuit 10 is shown as same would appear in a typical thermodilution catheter. In the catheter assembly the temperature sensing element 11 such as a thermistor is matched to a resistor network. In FIGS. 1, 2 and 3, the network is shown as resistor 14 since the network can be a single resistor 14 connected to the temperature sensing device 11 as shown. The reason for matching resistor 14 to temperature sensing device 11 involves maintaining a constant resistance ratio in the face of manufacturing variations of the device 11, between the resistance values of the device 11 at a given temperature (say 37° C.) and of resistor 14. Maintaining this resistance ratio is necessary because devices such as temperature sensor 11 will vary as much as plus or minus 15 percent and an adequately maintained ratio between resistance 11 and 14 over a given tolerance range assures accuracy and linearity of temperature measurement in spite of the fact that the devices such as thermistor 11 usually exhibit a strong nonlinear relationship between their resistance value and temperature.

FIG. 2 is representative of the circuit in which the catheter assembly 13 is used as the input for a current responsive instrumentation amplifier 15. Connection to the catheter assembly 13 are made at terminals 16 (for the thermistor branch) and 17 (for the resistor branch). Two currents of a predetermined ratio are injected into points 16 and 17 in FIG. 2 through very high value resistors 18 and 19. These currents, and others as may be provided by amplifier 15, leave the catheter assembly 13 at point 22 and are drained in the constant current source 22a which acts as a sink. All connections to catheter points 16, 17 and 22 are made through resistors with a resistance of 1 megohm or more. Some of these resistors, 20 and 21, are shown in FIG. 3, most are not shown. This practice is followed to allow failures in active devices like integrated circuits without exposing the catheter assembly 13 to high leakage currents.

In addition to measurement of temperature, circuits for catheter identification are also connected across terminals 16 and 17 of catheter assembly 13. These circuits operate at different times and independently of one another.

For normal cardiac output operation the temperature range for a patient on which same is used can be expected to be 26° to 43° C. so the center of that range is 34.5° C. The junction 22 of temperature sensing device 11 and resistor 14 is connected to the constant current source 22a. When the temperature at the thermistor 11 is 34.5° C. no currents flow into or out of current responsive instrumentation amplifier 15. This is so because the ratio for resistors 18 and 19 matches that of the resistances of catheter assembly 13. Moreover the value of the resistances used makes the voltage at terminals 16 and 17 halfway between plus and minus five volts. If the temperature is not at 34.5° C. then the ratio of resistances 11 and 14 does not match the ratio of resistance 19 and 18. Current excesses or shortages are made up by amplifier 15. Therefore, current flowing into or out of the current responsive instrumentation amplifier is indicative of the temperature difference at thermistor 11 of the catheter assembly 13. Over the operating range of 26° to 43° C. the currents in and out of current responsive instrumentation amplifier 15 are essentially proportional to the temperature at the thermistor 11.

In FIG. 1, the temperature sensing circuit 10 is shown as it would appear in a typical catheter. The matching resistor network is a single resistor 14. This resistor is chosen so that if the temperature of thermistor 11 is 37.0° C., the ratio of the resistance values of thermistor 11 and resistor 14 are optimum for the purpose of linearizing the non-linear response to temperature of thermistor 11. That means that, if the resistance of thermistor 11 at 37.0° C. is about 10 percent lower than nominal, then the resistance of resistor 14 would also be 10 percent lower than its value would be if it were to match a nominal value.

In FIG. 2 is shown the preferred method in which the circuit of FIG. 1 is used in the front end of a cardiac output computer. Terminal 22 is connected to the constant current source 22a which ultimately drains all current flowing through thermistor 11 and resistor 14 to the minus 5 volt rail of the analogue power supply.

The currents through thermistor 11 and resistor 14 are sourced by the plus 5 volt rail of the analogue power supply. The ratio of the resistance values of resistor 19 and 18 matches that of the resistances of thermistor 11 and resistor 14 when thermistor 11 is at 34.5° C. 34.5° C. is the midway point of the temperature range for which most cardiac output computers are designed, i.e, 26° to 43° C. At that temperature the voltage at terminal 16 will be exactly halfway between the plus 5 volt rail and the minus 5 volt rail of the analogue power supply. This halfway point is also referred to as analogue ground. Similarly the resistance of resistor 18 is such that the current through resistor 18 equals the current through resistor 14 when thermistor 11 is at 34.5° C. and the voltage at terminal 17 is also exactly at analogue ground. The input terminals 16 and 17 of the current responsive amplifier 15 are maintained at analogue ground by the amplifier circuit. Therefore, when thermistor 11 is at 34.5° C., no current will flow into or out of the terminals 16 and 17 of amplifier 15.

If thermistor 11 is not at 34.5° C. but between 26° C. and 43° C., currents will flow into or out of the terminals 16 and 17 of amplifier 15 and these currents are essentially proportional to the difference between the actual temperature of thermistor 11 and 34.5° C.

In FIG. 3, additional details of the temperature measuring circuits are shown, as well as details of the identification circuits and the means by which the circuit can be switched from measuring the temperature of thermistor 11 to determining the identity of the catheter assembly 13. To permit determination of the identity of catheter assembly 13 a capacitor 25 has been added to catheter circuit 13. This capacitor 25 will have a unique value that corresponds to the type of catheter. That is to say that, each catheter assembly 13 type is associated with a particular value of capacitor 25.

As mentioned before, amplifier 15 maintains a voltage equal to analogue ground at its input terminals 16 and 17. This is accomplished as follows. Input terminals 16 and 17 are each connected to the inverting input of operational amplifiers 15a and 15b. These inputs draw essentially no current. A resistor is connected between the inverting input of each amplifier to its output. Therefore, any current that flows into or out of the inputs to amplifiers 15a or 15b, actually flows into or out of the resistor that connects to the respective amplifier 15a or 15b output. If this current causes the inverting input to differ in voltage from the non-inverting input, the output of the amplifier 15a or 15b swings in a direction that will maintain essentially zero volts between the inverting and non-inverting inputs. Because the non-inverting input is connected to analogue ground, the inputs 16 and 17 are maintained at analogue ground. The outputs of amplifiers 15a and 15b are combined in a conventional analogue adding circuit (not shown) to produce a single voltage that is essentially proportional to the difference between the temperature of thermistor 11 and 34.5° C.

In spite of the high resistance values used in the instrumentation amplifier 15 input stages, the impedance levels at terminals 16 and 17 are very low and the voltage levels are, as explained, exactly halfway between the plus and minus 5 volts. It should be emphasized that this "halfway" voltage level, which could be referred to as analogue ground, is in reality very well insulated from actual ground, such as may be represented by a metal cold water pipe. In addition, terminals 16 and 17 are not directly connected to the halfway point, referred to as analogue ground, but through very high resistance values. However, the dynamic resistance between terminals 16 and 17 and analogue ground is very low, only on the order of a few ohms. The voltages at terminals 16 and 17 are very nearly equal to within a fraction of a volt (i.e., 0.001 volts), and input impedances of the instrumentation input stages as measured at terminals 16 and 17 are very small (i.e. 10 ohms).

FIG. 3 shows the specifics of the invention. Capacitor 25 connected between terminal 16 and 17 of the catheter assembly 13 does not affect normal temperature measurement operation of the catheter assembly 13 during a thermodilution cardiac output analysis. This is so because the voltage difference between terminals 16 and 17 is very small and stays so over the entire thermodilution temperature range. The low dynamic input impedances of the current responsive instrumentation amplifiers 15a and 15b create a time constant when combined with capacitor 25 that is very short when compared to the rate of which the blood temperature changes.

The identification of the catheter size is done by means of charging and discharging (charging in the opposite direction) of capacitor 25. The time for discharge is directly related to the capacitor value and each size of catheter includes a specifically valued capacitor 25. The time for discharge or decay of the full charged capacitor 25 will vary with temperature of thermistor 11, but the variance is within a known range for any specifically selected capacitor value. Each different value of capacitor 25 can be spaced on a time diagram such that its time for decay values for the entire temperature range is well separated from the range of any other selected capacitor 25. For the present and preferred embodiment this approach is adequate for the number of catheter types which need to be identified.

Each different gauge of catheter includes a specifically predetermined value for the capacitor 25, shown in FIG. 3. The capacitor 25 works in combination with the resistances of 11 and 14 to form a time constant. A different capacitance value will be read as a different decay time interval, and although the time interval for a specific gauge will vary with temperature; the range of variance can be accommodated. The particular gauges can be determined without concern for the variations due to temperature and tolerances. In the preferred embodiment that is the means by which a catheter gauge is identified. Should there be the need to determine a greater number of catheter gauges then an approach in which the temperature of thermistor 11 is also determined and applied to achieve a reduction in the variation of the time constant due to temperature can be used. In the present situation that is not necessary.

FIG. 3 shows that four switches, 26, 27, 28, and 29 are connected in the circuit. When the circuit must serve to measure the temperature of thermistor 11 all switches are closed as shown. When it is desired to determine the identity of the catheter, switches 27, 28 and 29 are opened simultaneously; switch 26 is retained as shown.

The opening of switches 27, 28 and 29 results in the following changes. Switch 27 disconnects the current flowing through resistor 18, which assures that amplifier 15a will not be overloaded and will be able to maintain terminal 17 at analogue ground. Switches 28 and 29 disconnect the catheter assembly 13 from the rest of the analogue circuit allowing the current through resistor 19 to charge capacitor 25. The final voltage to which capacitor 25 is charged is determined by the voltage divider formed by resistor 19; thermistor 11 and resistor 14.

Switch 26 is arranged to be either connected to plus 5 volts or to minus 5 volts. In the former condition, current flows through resistor 19 for a period of time controlled by the digital section microprocessor circuit 30 which includes the counter or timer 24. Timer 24 permits current to flow for a specified time period $t_o$ sufficient to permit current flow through capacitor 25 until same is fully charged and has reached its equilibrium, see FIG. 4. At equilibrium terminal 16 will assume a small voltage (typically 30 millivolts) above the voltage at terminal 17.

In the preferred embodiment, this period of time $t_0$ is approximately 0.2 seconds. After the full charge of capacitor 25 has been attained, digital section microprocessor circuitry 30 moves switch 26 to 5 volts negative and starts the timer 24 from a reset condition. Timer 24 measures the amount of time $t_1$ minus to for the charged capacitor 25 to discharge to zero volts, see FIG. 4. The time required for this discharge is indicative for the particular capacitor value and therefore of the catheter gauge because the value of the capacitor 25 is such that same is specifically selected for each given catheter gauge.

A comparator 23 is used to stop the timer 24 when the discharge curve, FIG. 4, passes through zero volts at $t_1$, after decay of the charge of capacitor 25. The comparator 23 has a high common mode rejection ratio to help ignore the presence of noise such as hum, from the transduced signal of catheter assembly 13 as seen at terminals 16 and 17. The voltage across capacitor 25 does not change due to hum and therefore the comparator 23 is accurate even with the presence of noise.

When the voltage at terminal 16 is equal to that at terminal 17, this condition can be detected by the comparator 23. When the voltage at terminal 16 drops below the voltage at terminal 17, the output of the comparator 23 goes from high to low and stops a timer 24. Timer 24 is connected to the output 23a of comparator 23. The value read on the timer 24 is indicative of the type of catheter assembly 13 used. Each type of catheter assembly 13 has a capacitor 25 connected between terminals 16 and 17 and the value of capacitance for capacitor 25 is unique for each type of catheter assembly 13.

It is to be expected that for a given type of catheter assembly 13, the indicative time interval will vary with the temperature as sensed by temperature sensing device 11 and with the value of resistor 14 as the result of the matching process. Therefore, it is necessary to assign a range of times for each size of catheter assembly 13 and to space the values of capacitance of capacitor 25 (used for each size) far enough apart so that each catheter assembly 13 type can be positively recognized in spite of these expected variables. The preferred factor of 3 allows for all these variables, but different applications may require another factor.

In particular, the time needed to discharge the capacitor 25 can be calculated knowing the resistances of the temperature sensing device 11 and the resistor 14 and the capacitance of capacitor 25. The following chart shows the differences in the time function as a result of different capacitances.

| Added Capacitance Picofarads (pF) | Approximate Time (Microseconds) | |
| --- | --- | --- |
| 0 |  | <100 |
| 10,000 | 180 | 360 |
| 33,000 | 600 | 1200 |
| 100,000 | 1800 | 3600 |
| 330,000 | 6000 | 12000 |

Zero added capacitance will be a competitive catheter or a catheter for which no constants have been included in the software. The four capacitance values given above can be assigned to four different catheter gauges as follows:

| Catheter Gauge: | 1 | Capacitance | .01 microfarad |
| --- | --- | --- | --- |
| | 2 | | .033 microfarads |
| | 3 | | .1 microfarads |
| | 4 | | .33 microfarads |

Once this determination has been made, the time measured by timer 24 can be used as an input signal to the current responsive instrumentation amplifier 15 and more specifically to set the value of catheter lumen size into the cardiac output computer of which amplifier 15 is a portion.

The invention consists of the addition of a capacitor 25 between terminals 16 and 17 of the catheter assembly 13 and the additional of instrumentation circuitry and software to allow the measurement of a time constant created by the capacitor 25 under special circumstances. These special circumstances are set up by switches 26 through 29 (see FIG. 3 for placement of these switches in the preferred circuit). The input signals at comparator 23 from terminals 31 and 32 are measured only as a difference between them thus effectively filtering any hum from the catheter assembly 13. An optical coupler 33 is connected to the output 23a as a safety device to electrically isolate the catheter assembly 13 from the digital section microprocessor circuitry 30.

While a specific and preferred embodiment has been shown and described for use in connection with thermodilution catheters and cardiac output computers, skilled artisans will no doubt appreciate that the technique disclosed herein can be used in connection with other equipment so long as it is understood that the timing of a capacitor discharge is the requisite element used for identification of the nature of the remote element. More specifically, this technique can be used in conjunction with other circuitry without the need of additional connecting terminals, wires, leads and the like. Thus, a simplified approach to automatic identification is provided without the addition of a complex network or wiring schemes and without interference with the measurement of the transduced signal, in this case a thermodilution wave form. In the claims which follow, the basic concept is sought to be protected apart from the specific preferred disclosure.

What is claimed:

1. A thermodilution catheter and cardiac output computer system comprising:
   a catheter having a distal and a proximal end, with a temperature sensing means at said distal end and and a lumen extending between the ends of the passage of a bolus during a thermodilution procedure;
   a catheter identification means at said proximal end as part of a cardiac output computer;
   a cardiac output computer microprocessor circuit responsive to the temperature sensing means in the catheter;
   a thermistor and resistor as part of the temperature sensing means;
   a capacitor at the distal end of the catheter, the capacitor of a predetermined value selected to indicate a characteristic of said catheter; said capacitor in circuit with said temperature sensing means and the capacitor arranged for being charged in both directions;
   said microprocessor circuit at the proximal end including switching circuit means for selectively and automatically charging said capacitor to equilibrium and thereafter connecting said capacitor to discharge;
   a timer in said microprocessor circuit activated at a time after said capacitor is fully charged to equilibrium and thereafter stopped when said capacitor is discharged to a point of zero charge, and
   an analysis means in said microprocessor circuit connected to said timer for monitoring a measured time interval of capacitor discharge and ascribing a thermodilution catheter characteristic comparable to standards programmed into said microprocessor circuit.

2. The thermodilution catheter of claim 1 including a network of resistance means in circuit with said thermistor and as part of said temperature sensing means to establish a constant resistance ratio assuring linearity of signal from said thermistor over a predetermined temperature range.

3. The thermodilution catheter of claim 2 wherein said linearity of signal from said catheter is assured through said range by selection of said resistor connected in the circuit of said temperature sensing means.

4. The thermodilution catheter of claim 3 wherein a temperature range in which the catheter operates is accounted for by choices of capacitor values sufficient to space the measured time interval for each characteristic apart adequately to compensate for temperature variation of the catheter within said range.

5. The thermodilution catheter of claim 2 wherein said switching circuit means connect a constant current power source to said capacitor for fully charging said capacitor through a voltage divider formed by the network of resistance means and then switching the charged capacitor to automatically discharge said capacitor by allowing current to flow in a direction opposite to the current flow to fully charge so the capacitor attains at least a zero voltage condition of charge.

6. The thermodilution catheter of claim 1 wherein said microprocessor circuit includes in circuit therewith a comparator means connected across the capacitor for controlling said timer.

7. The thermodilution catheter of claim 5 wherein said comparator means includes means to feed the output thereof into said microprocessor circuit to stop said timer upon receiving an input change from said capacitor.

8. The thermodilution catheter of claim 6 wherein said comparator means has a high common mode rejection ratio to ignore all but the change of the input from said catheter whereby the charge on said capacitor can be used to start and stop said timer.

9. A process for using a thermodilution catheter assembly having a thermistor, resistance network and a capacitor in circuit therewith and a cardiac output computer system including the following steps:
   connecting the catheter assembly across a current responsive instrumentation amplifier input terminals,
   adding and removing resistance connected to the input terminals for adjusting and maintaining a potential difference between the input terminals and analogue ground,
   connecting a constant current supply to the catheter assembly to fully charge said capacitor and cause the voltage at both input terminals to be substantially identical
   disconnecting a constant current supply to the catheter assembly to permit voltage between the terminals connected to said thermistor,
   discharging the fully charged capacitor in a direction opposite to that for fully charging to achieve at least a zero voltage, and
   measuring a time interval for discharge of the capacitor to the zero voltage.

10. The process of claim 9 with the additional step of using the measured time interval as a signal for identification of the capacitor value.

11. The process of claim 10 with the additional step of selecting the measured time interval as a function of temperature and the capacitor value thus separating time intervals for different capacitor values sufficiently to allow for temperature difference.

12. The process of claim 9 with the additional step of using the time interval measured as input to a comparator connected across an output from the catheter assembly to start and stop the time interval measurement.

* * * * *